(12) United States Patent
Kim et al.

(10) Patent No.: US 12,138,038 B2
(45) Date of Patent: Nov. 12, 2024

(54) WEARABLE GAIT START INTENTION DETECTION DEVICE

(71) Applicant: KOREA INSTITUTE OF SCIENCE AND TECHNOLOGY, Seoul (KR)

(72) Inventors: Choong Hyun Kim, Seoul (KR); Jinmyeong Lee, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 632 days.

(21) Appl. No.: 17/105,503

(22) Filed: Nov. 26, 2020

(65) Prior Publication Data
US 2021/0153775 A1    May 27, 2021

(30) Foreign Application Priority Data

Nov. 27, 2019   (KR) .......................... 10-2019-0154639

(51) Int. Cl.
*A61B 5/103*    (2006.01)
*A61B 5/00*     (2006.01)
*A61B 5/11*     (2006.01)

(52) U.S. Cl.
CPC .......... *A61B 5/1038* (2013.01); *A61B 5/0002* (2013.01); *A61B 5/112* (2013.01); *A61B 5/6807* (2013.01)

(58) Field of Classification Search
CPC ..... A61B 5/1038; A61B 5/0002; A61B 5/112; A61B 5/6807; A61B 2562/0219;
(Continued)

(56) References Cited

U.S. PATENT DOCUMENTS

2005/0131317 A1* 6/2005 Oddsson .............. A61B 5/4561
                                                            600/592
2012/0035509 A1* 2/2012 Wilson ................. A61B 5/6807
                                                            600/592
(Continued)

FOREIGN PATENT DOCUMENTS

KR    1020160020279 A    2/2016
KR    1020190118265 A    10/2019

OTHER PUBLICATIONS

Huanghe Zhang et al., "Estimating CoP Trajectories and Kinematic Gait Parameters in Walking and Running Using Instrumented Insoles," IEEE Robotics and Automation Letters, Oct. 2017, pp. 2159-2165, vol. 2, No. 4.
(Continued)

*Primary Examiner* — Patrick Fernandes
(74) *Attorney, Agent, or Firm* — CANTOR COLBURN LLP

(57) ABSTRACT

Disclosed is a gait start intention detection device for detecting a walker's gait start intention, including a plurality of left foot sole sensor units and a plurality of right foot sole sensor units to measure ground reaction force signals generated from foot soles while walking, and a calculation unit to receive and calculate the left ground reaction force signal and the right ground reaction force signal, wherein the calculation unit calculates a center of pressure (COP) location in a walking direction and a direction perpendicular to the walking direction using data of the ground reaction force signal measured from each sensor unit, and detects the walkers gait start intention when a ground reaction force of a swing foot heel of the walker increases, and at the same time, the COP location moves to a rear side of the walker.

8 Claims, 7 Drawing Sheets

(58) Field of Classification Search
CPC .......... A61B 2562/0247; A61B 5/1036; A61B 2505/09; A61B 5/6829; A61B 5/1123; A61B 5/1121; A61B 5/4023; A61H 2201/5061; A43B 3/34; G16H 20/30
See application file for complete search history.

(56) References Cited

U.S. PATENT DOCUMENTS

| | | | |
|---|---|---|---|
| 2012/0092169 A1* | 4/2012 | Kaiser | G16H 50/20 600/587 |
| 2016/0007885 A1* | 1/2016 | Basta | A61B 5/112 600/595 |

OTHER PUBLICATIONS

Veronica Cimolin et al., "Gait initiation and termination strategies in patients with Prader-Willi syndrome," Journal of NeuroEngineering and Rehabilitation, 2017, pp. 1-8, vol. 14, No. 44.

* cited by examiner

COP location in gait initiation: SWHO, swing leg heel off; SWTO, swing leg toe off: STTO, stance leg toe off.

WEARABLE GAIT START INTENTION DETECTION DEVICE

CROSS-REFERENCE TO RELATED APPLICATION

This application claims priority to Korean Patent Application No. 10-2019-0154639, filed on Nov. 27, 2019, and all the benefits accruing therefrom under 35 U.S.C. § 119, the contents of which in its entirety are herein incorporated by reference.

TECHNICAL FIELD

The present disclosure relates to a gait start intention detection device for pre-detecting the gait start intention of a walker in a standing posture.

BACKGROUND ART

Seniors or disabled people with impaired mobility have difficulties in voluntary gait. In this case, gait assistive devices (or robots) may help them to improve the movements of the upper and lower limbs, and since it takes a predetermined amount of time to control the robots or assistive devices, it is necessary to detect a walker's gait start intention before the point in time at which the walker wants to walk.

However, according to previous studies, there are limitations due to sensors used to detect the gait start intention, and it is difficult to pre-detect the gait start intention.

Meanwhile, the human body maintains balance by the activation of specific muscles corresponding to an arbitrary activity prior to the change in posture caused by the activity. For example, when raising an arm in a standing posture, the muscles of the lower limbs are activated earlier than the muscles of the upper limbs to maintain body balance. Since unintentional muscle adjustments take place before an intentional movement begins, this is referred to as anticipatory postural adjustments (APAs).

The present disclosure proposes a device for detecting the gait start intention by detecting specific biosignals generated immediately before the start of walking by anticipatory postural adjustments in a standing posture.

RELATED LITERATURES

Patent Literatures (Patent Literature 1) Korean Patent Publication No. 10-2016-0020279

DISCLOSURE

Technical Problem

For example, as shown in FIG. 7, Patent Literature measures the vertical ground reaction forces on big toes and heels of both feet, and detects the gait start intention when the magnitude of the ground reaction force on a preceding leg exhibits a peak, and any one of a force plate with a force sensor and a force sensing resistor sensor is used as a sensor.

However, since Patent Literature detects the gait start intention when the magnitude of the ground reaction force on the sole of the foot exhibits a peak, in this case, it is possible to detect the gait start intention only when the walker moves to some extent, and thus it takes a long time to detect the gait start intention.

Accordingly, there is a need for development of control technology for a gait start intention detecting system for immediately detecting the gait start intention with ease-of-wear, low cost and high performance.

Technical Solution

To solve the above-described technical problem, the present disclosure provides a gait start intention detection device for detecting a walker's gait start intention, including a plurality of left foot sole sensor units to measure a left ground reaction force signal generated from a left foot sole while walking, a plurality of right foot sole sensor units to measure a right ground reaction force signal generated from a right foot sole while walking, and a calculation unit to receive and calculate the left ground reaction force signal and the right ground reaction force signal, wherein the calculation unit calculates a center of pressure (COP) location in a walking direction and a direction perpendicular to the walking direction using data of the ground reaction force signal measured from each sensor unit, and detects the walker's gait start intention when a ground reaction force of a swing foot heel of the walker increases, and at the same time, the COP location moves to a rear side of the walker.

Additionally, the calculation unit of the present disclosure may identify a gait phase by calculating the COP location and left and right feet COP locations and their ratio from the ground reaction force signal.

Additionally, when transmitting the data of the left foot sole sensor units and the right foot sole sensor units of the present disclosure, the data may be transmitted from any one of the left foot sole sensors and the right foot sole sensors to the other, combined together and transmitted to the calculation unit, or the data of the left foot sole sensor units and the right foot sole sensor units may be each transmitted to the calculation unit and combined together.

Additionally, the COP location of the present disclosure and the ratio of respective COP in each foot sole may be readable in real time through a smart device.

Additionally, the gait start intention detection device of the present disclosure may further include an amplifier to amplify the left ground reaction force signal and the right ground reaction force signal.

Additionally, the gait start intention detection device of the present disclosure may further include a timer to synchronize the left ground reaction force signal with the right ground reaction force signal.

Additionally, the plurality of left foot sole sensors and the plurality of right foot sole sensors of the present disclosure may be respectively installed in big toes, 1st metatarsal bones, 5th metatarsal bones, cuboid bones and heels of the left foot and the right foot.

Advantageous Effects

The present disclosure acquires and analyzes ground reaction force information generated while walking using force sensors (force sensing resistors (FSRs)) installed on the bottom of the insole, and detects the location and time at which the ground reaction force is generated and the movement of the center of pressure (COP) in real time based on the information.

Accordingly, the present disclosure provides information necessary to control a gait assistive device by pre-detecting the gait start intention.

BEST MODE

Hereinafter, a gait start intention device and an analysis method using the same according to an embodiment of the present disclosure will be described in detail through the preferred embodiments of the present disclosure with reference to the accompanying drawings.

Prior to description, unless the context clearly indicates otherwise, the term "comprises" when used in this specification, specifies the presence of stated elements, but does not preclude the presence or addition of one or more other elements.

Although the embodiments of the present disclosure are described with reference to the accompanying drawings, this is described for illustration, and the technical spirit of the present disclosure and the elements and operation are not limited thereto.

Figure 1:
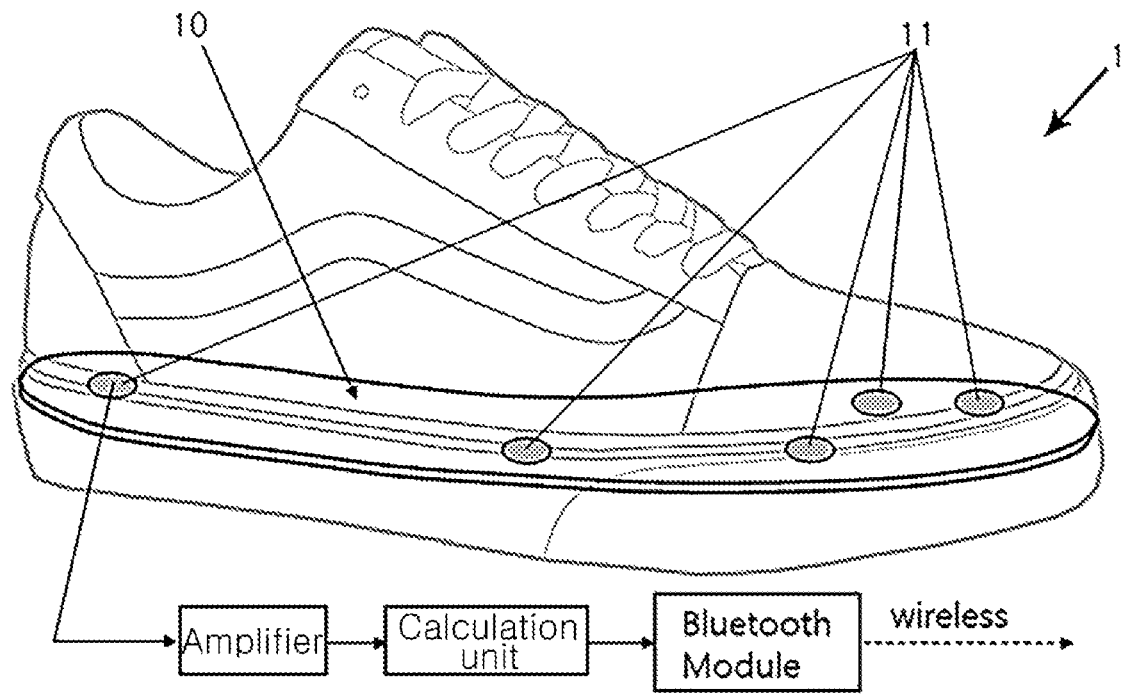
FIG. 1 is a diagram schematically showing a gait start intention detecting device according to an embodiment of the present disclosure.
Figure 2:
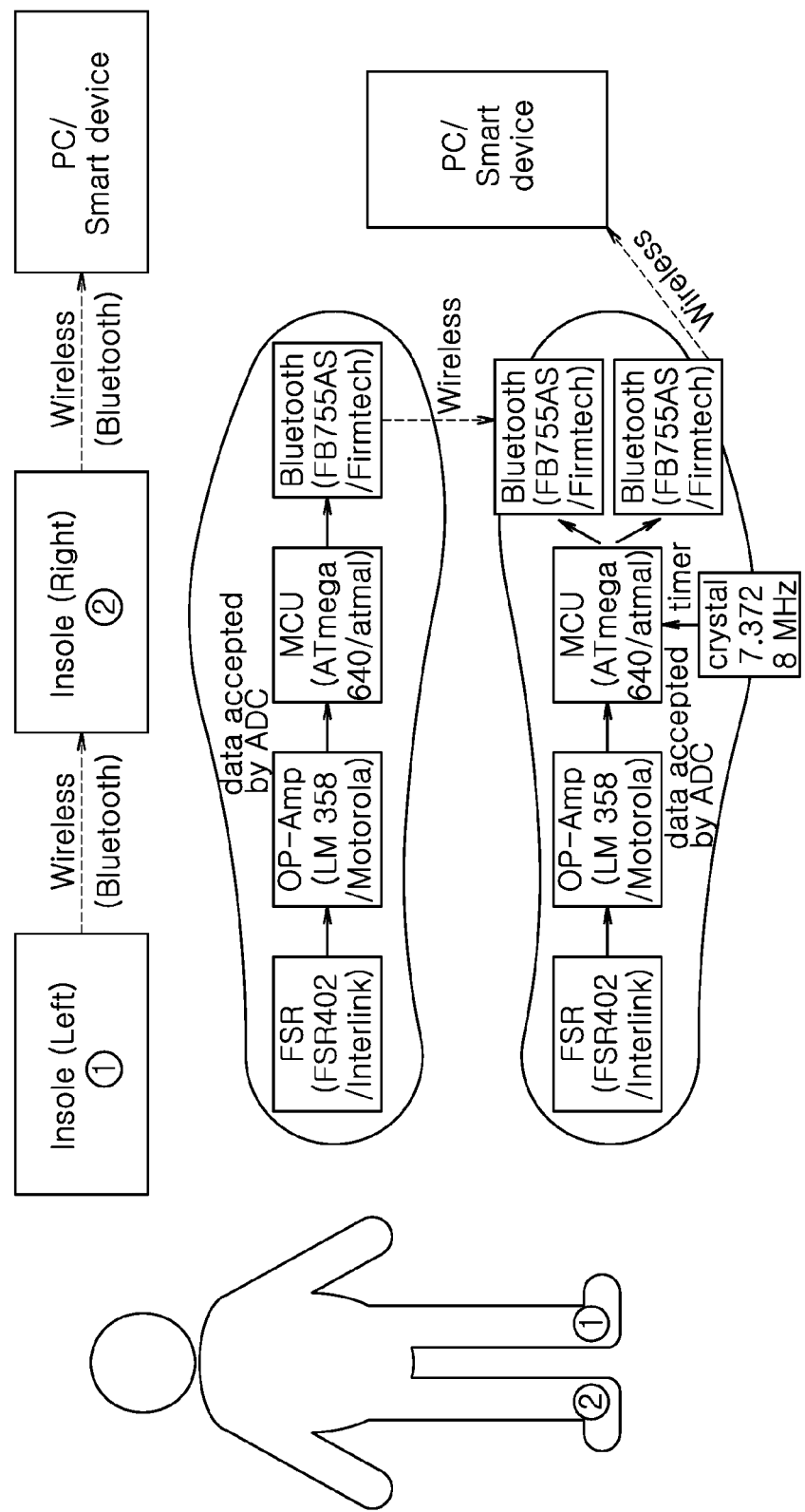
FIG. 2 is a diagram illustrating a configuration of a gait start intention detection device according to an embodiment of the present disclosure.

FIG. 1 is a diagram schematically showing a gait start intention detecting device 1 according to an embodiment of the present disclosure, and FIG. 2 is a diagram illustrating the configuration of the gait start intention detection device 1 according to an embodiment of the present disclosure.

In general, both feet soles of the human body repeatedly contact and push off the ground in an alternating manner while walking. Accordingly, in general, the ground reaction force occurs on both feet soles while standing or walking, and the gait start intention detecting device 1 according to an embodiment of the present disclosure detects the gait start intention based on the ground reaction force and a change in the center of pressure (COP) location calculated from the ground reaction force.

As shown in FIG. 1, the gait start intention detecting device 1 according to an embodiment of the present disclosure includes force sensors (force sensing resistors) 11 attached to the bottom of an insole 10 on the inside of a shoe and uses five sensors 11 in each of both feet, and the measured ground reaction force data is amplified by an amplifier and summed up in a calculation unit.

This process is the same with the left foot and the right foot. Data collected by a calculation processing device of the left foot may be wirelessly transmitted to the right foot through a Bluetooth device, and the calculation unit calculates the ground reaction force data of the right foot and combines with the ground reaction force data collected from the left foot.

In this case, the ground reaction force data of both feet may be synchronized using time data from a separate timer. That is, the synchronization process is performed to minimize a difference in data measurement time between both feet by applying the external timer, thereby achieving continuous gait start intention analysis.

Subsequently, the calculation unit detects the gait start intention using the ground reaction force data, or by calculating COP from the data. The result may be transmitted to a computer or a smart device for gait start intention analysis through the Bluetooth device. Where necessary, the result or a trigger signal for control may be transmitted to an external device, for example, a gait assistive device through a wired/wireless device.

Figure 3:
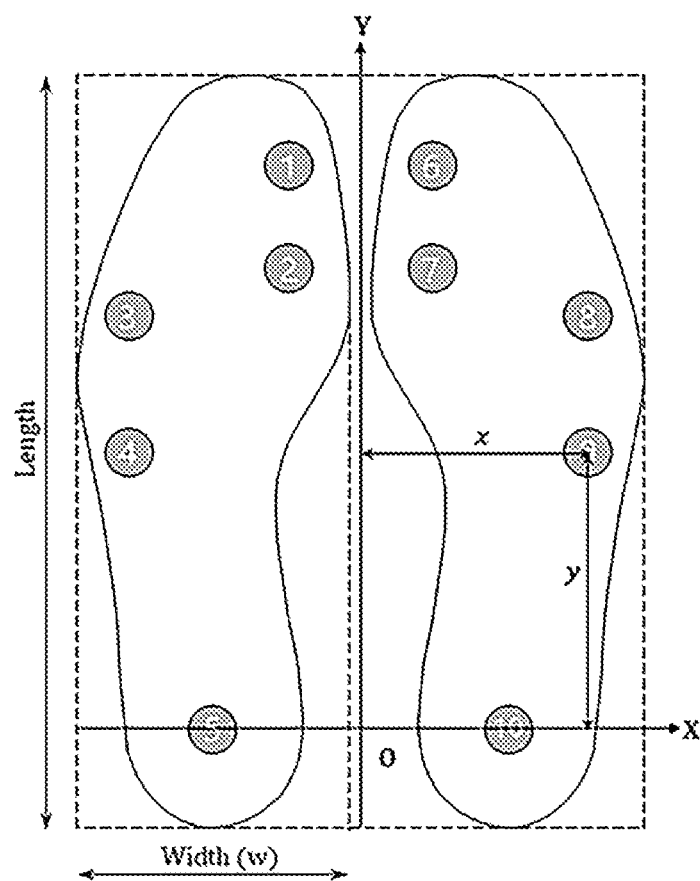
FIG. 3 is a diagram illustrating a sensor attachment location of a gait start intention detection device according to an embodiment of the present disclosure.

FIG. 3 is a diagram illustrating the sensor attachment location of the gait start intention detection device according to an embodiment of the present disclosure.

As shown in FIG. 3, the force sensors 11 installed on the bottom of the insole 10 to measure the ground reaction force are attached to a total of five locations, namely, big toe, 1st metatarsal bone, 5th metatarsal bone, cuboid bone and heel that touch the ground in a sequential order for each phase of gait.

The gait start intention detection device 1 according to an embodiment of the present disclosure acquires the ground reaction force using the standardized insole having the force sensors installed therein, taking into account the wearer's foot size and joint location in the foot, and calculates the COP from the data, thereby acquiring the ground reaction force data and COP data with high consistency irrespective of the wearer's foot size or body weight.

In FIG. 3, a line connecting the centers of heels of both feet is shown as x axis, and a direction indicating the walking direction passing through the center between both feet is shown as y axis.

The COP may be calculated as below using the ground reaction force data generated while walking.

$$COP_X = \sum_{i=1}^{10} FSR_i \times x_i \Big/ \sum_{i=1}^{10} FSR_i$$

$$COP_Y = \sum_{i=1}^{10} FSR_i \times y_i \Big/ \sum_{i=1}^{10} FSR_i$$

Here, $COP_X$ and $COP_Y$ denote a location in each walking direction (y axis) of the combined COP reflected on the ground with the movements of both feet while walking and a location in a direction (x axis) perpendicular to the walking direction.

Additionally, the present disclosure may calculate the combined COP and the left and right feet COP locations and their ratio from the ground reaction force signal, and considering them, additionally identify the gait phase of the walker.

Figure 4:
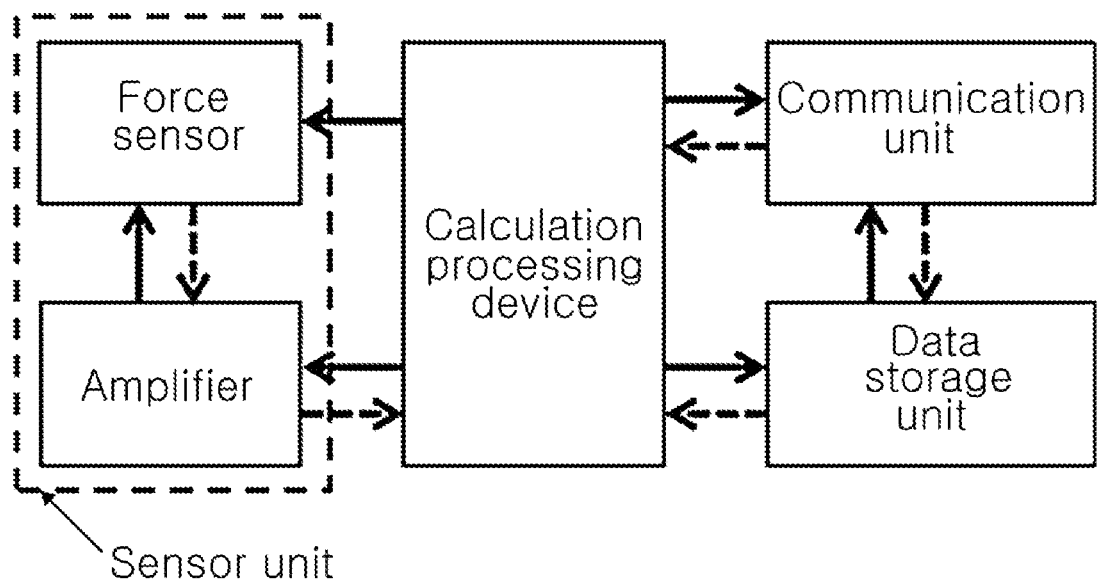
FIG. 4 is a flowchart showing the operation process of a gait start intention detection device according to an embodiment of the present disclosure.
Figure 5:
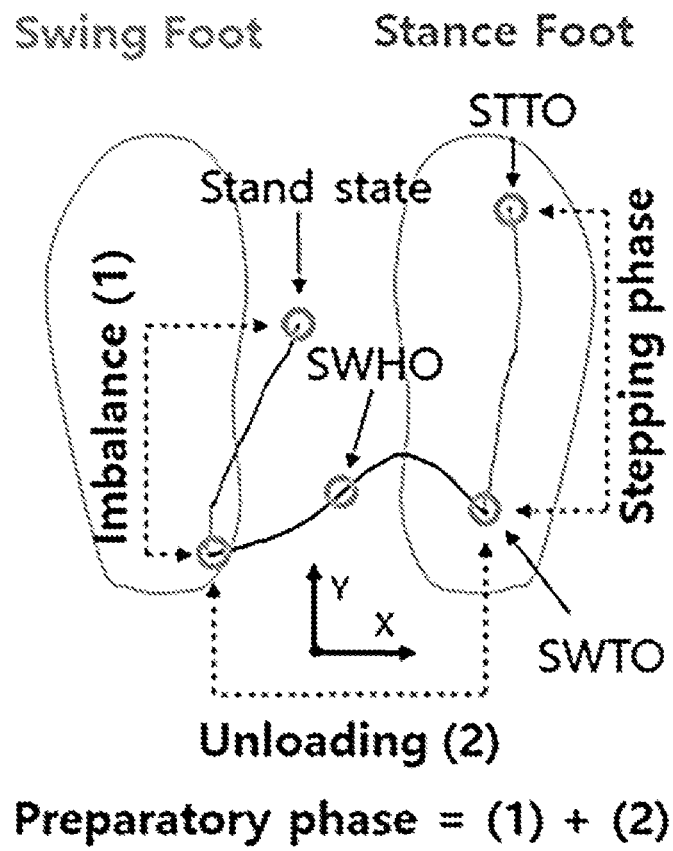
FIG. 5 is a graph showing a trajectory of a center of pressure (COP) location in the phase of gait initialization including an anticipatory postural adjustment phase, in the application of a gait start intention detection device according to an embodiment of the present disclosure.

FIG. 4 is a flowchart showing the operation process of the gait start intention detection device 1 according to an embodiment of the present disclosure, and FIG. 5 is a graph showing the trajectory of COP location at the phase of gait initialization including the anticipatory postural adjustment phase, in the application of the gait start intention detection device 1 according to an embodiment of the present disclosure.

As shown in FIG. 5, shown is a change in COP occurring at the phase of gait initialization from the standing state.

In detail, when the gait intention occurs from the standing state, gait initialization is performed through the imbalance phase in which the COP moves to the swing foot heel on the rear side of the human body opposite to the walking direction, and subsequently, the unloading phase in which the COP moves to the stance foot again and the swing foot heel is lifted up.

The imbalance phase and the unloading phase is collectively referred to as a preparatory phase. The gait start intention detection device according to an embodiment of the present disclosure can detect the gait start intention before the imbalance phase ends, thereby ensuring sufficient time for controlling an external device such as a gait assistive device, i.e., the lead time.

Figure 6:
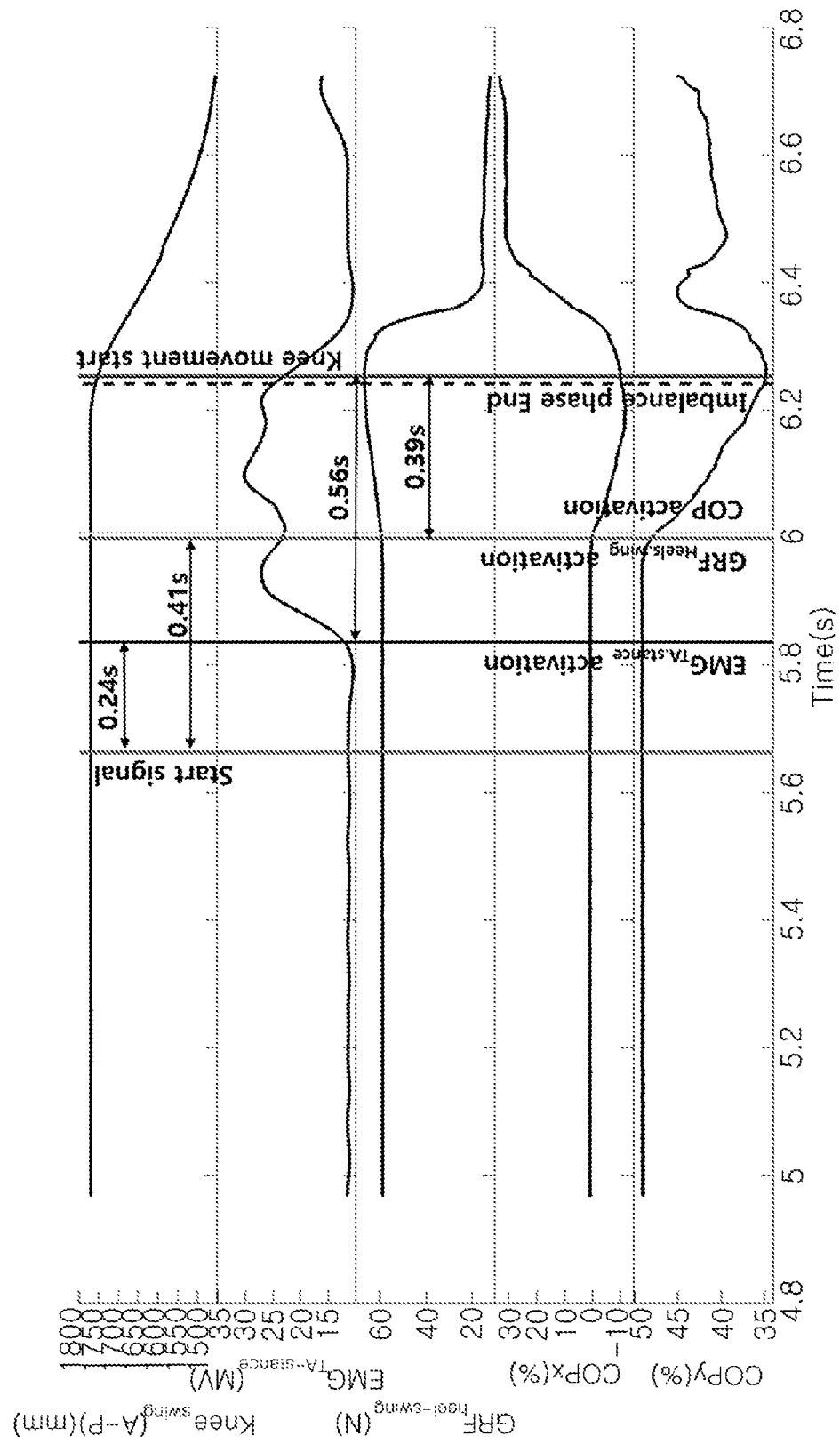
FIG. 6 shows a comparison of biosignal data acquired through a gait experiment by applying a gait start intention detection device according to an embodiment of the present disclosure.
Figure 7:
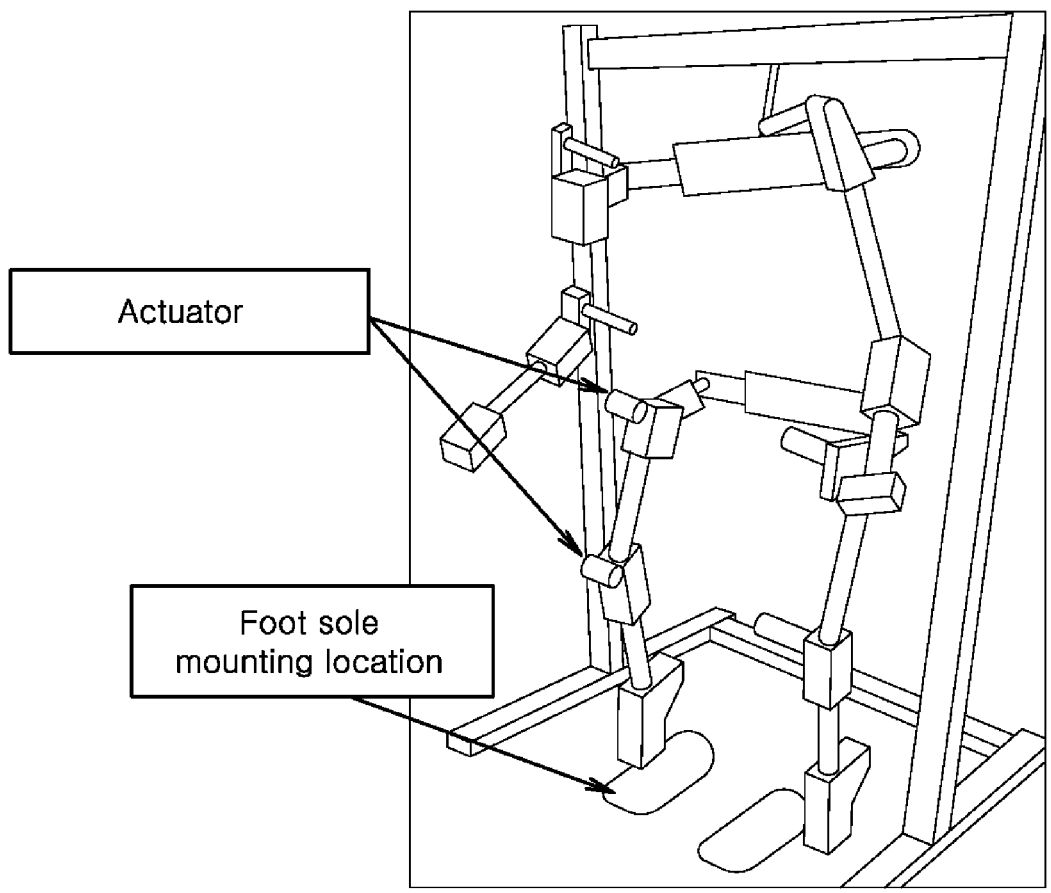
FIG. 7 is a photographic image schematically showing a gait start intention detection device according to the related art.

FIG. 6 shows a comparison of biosignal data acquired through a gait experiment by applying the gait start intention detection device 1 according to an embodiment of the present disclosure, and specifically, in the experiment in which the walker in a standing state starts walking upon seeing a start signal (red line), biometric data generated from the human body of the walker is shown.

FIG. 6 shows the ground reaction force measured by the gait start intention detection device 1 according to an embodiment of the present disclosure, biosignals (electromyogram (EMG) signals) acquired from EMG sensors attached to shin muscles (anterior tibialis muscle), COPx and COPy, and human body motion data using a motion capture system for verifying the data are shown. The point in time at which the walker actually starts walking is detected by attaching markers to the knee of the stance foot and tracking the movements using the motion capture system, and the start of gait is detected by the movement of the knee.

Seeing the details shown in FIG. 6, it takes 0.8 s on the average from the point in time at which the start signal (red line in FIG. 6) indicating the start of gait is generated to the point in time at which the knee actually moves. Meanwhile, the shin muscle signal of the stance foot shows a change at 0.24 s, the ground reaction force of the swing foot heel at 0.41 s, and COPx and COPy locations at about 0.41 s to 0.42 s.

Accordingly, it can be seen that biosignals by anticipatory postural adjustments are generated in multiple body parts before the walker actually moves.

That is, there is a time interval, i.e., the lead time, between 0.38 s to 0.56 s from the point in time at which biosignals by anticipatory postural adjustments are generated to the point in time at which the knee of the swing foot actually moves, and it is much longer than the time required to control an external device, for example, a gait assistive device.

Accordingly, the use of biosignals by anticipatory postural adjustments makes it possible to control the gait assistive device at a desired time.

Meanwhile, referring to the previous research results, the inter-item correlation coefficients of EMG signals of shin muscles measured using the EMG sensors and COP data measured by the force plate range from 0.42 to 0.64 and from 0.6 to 0.63 respectively.

However, consistency between the ground reaction force of the swing foot heel measured by the gait start intention detecting device 1 according to an embodiment of the present disclosure and COPx and COPy data is about 0.8 to 0.95 and about 0.8 to 0.96 respectively, and it can be seen that consistency of biometric data for detecting the gait start intention acquired by the device according to an embodiment of the present disclosure is higher.

Here, the inter-item correlation coefficient is a measure of similarity of the same type of biometric data acquired from the same subject, and the value closer to 1 indicates higher consistency. That is, it represents high data reproducibility by repeated experiments.

Accordingly, the gait start intention detecting device according to the present disclosure detects the gait start intention when the ground reaction force of the swing foot heel increases, and at the same time, COPy moves to the rear side of the human body, and in this case, it can be seen that the detection success rate is significantly higher than the related art.

In view of the foregoing description, those skilled in the art will understand that the present disclosure may be embodied in other specific forms without changing the technical spirit or essential features thereof.

Therefore, it should be understood that the embodiments as described hereinabove are provided for illustration purposes, but not intended to limit the present disclosure to the disclosed embodiments, the scope of the present disclosure is defined by the appended claims rather than the foregoing detailed description, and it should be interpreted that the scope of the present disclosure covers all changes or modifications derived from the meaning and scope of the appended claims and their equivalent concept.

INDUSTRIAL APPLICABILITY

The present disclosure provides a wearable gait start intention detection device, and can be used to develop low-cost and high-performance gait assistive devices or rehabilitation medical devices for patients or elderlies in need of gait rehabilitation.

DETAILED DESCRIPTION OF MAIN ELEMENTS

1: Gait start intention detection device
10: Insole
11: Sensor

The invention claimed is:

1. A gait start intention detection device for detecting a walker's gait start intention, comprising:
   a plurality of left foot sole sensor units configured to measure a left ground reaction force signal generated from a left foot sole while walking;
   a plurality of right foot sole sensor units configured to measure a right ground reaction force signal generated from a right foot sole while walking; and
   a calculation unit configured to receive and calculate the left ground reaction force signal and the right ground reaction force signal,
   wherein the calculation unit is configured to calculate a first center of pressure (COP) location in a walking direction and a second COP location in a direction perpendicular to the walking direction using the left ground reaction force signal and the right ground reaction force signal, and the calculation unit is further configured to detect the walker's gait start intention when a respective ground reaction force signal of the left ground reaction force signal and the right ground reaction force signal of a swing foot heel of the walker increases, and at a same time, the first COP location moves to a rear side of the walker, the swing foot heel comprising one of a left foot heel and a right foot heel of the walker; and wherein the gait start intention detection device is configured to transmit, responsive to detecting the walker's gait start intention, a control signal to a gait assistive device before an imbalance phase ends, the imbalance phase defining a period in which the first COP moves to the swing foot heel on the rear side of the walker opposite to the walking direction.

2. The gait start intention detection device according to claim 1, wherein the calculation unit identifies a gait phase from a combined COP location comprising the first COP location and the second COP location and a ratio of the first COP location and the second COP location to the left ground reaction force signal and the right ground reaction force signals.

3. The gait start intention detection device according to claim 1, wherein when transmitting data comprising the left ground reaction force signal and the right ground reaction force signal of the plurality of left foot sole sensor units and the plurality of right foot sole sensor units, the data is transmitted from any one of the plurality of left foot sole sensors to a right foot sole sensor or from any one of the plurality of right foot sole sensors to a left foot sole sensor, combined together, and transmitted to the calculation unit.

4. The gait start intention detection device according to claim 1, wherein data comprising the left ground reaction force signal and the right ground reaction force signal of the plurality of left foot sole sensor units and the plurality of right foot sole sensor units is each transmitted to the calculation unit and combined together.

5. The gait start intention detection device according to claim 2, wherein the combined COP location and the ratio are readable in real time.

6. The gait start intention detection device according to claim 5, further comprising:
   an amplifier to amplify the left ground reaction force signal and the right ground reaction force signal.

7. The gait start intention detection device according to claim 6, further comprising:
   a timer to synchronize the left ground reaction force signal with the right ground reaction force signal.

8. The gait start intention detection device according to claim 7, wherein the plurality of left foot sole sensors and the plurality of right foot sole sensors are respectively installed in an insole below respective big toes, 1st metatarsal bones, 5th metatarsal bones, cuboid bones and heels of a left foot and a right foot of a subject.

* * * * *